(12) United States Patent
Cuevas (10) Patent No.: US 10,548,766 B2
(45) Date of Patent: *Feb. 4, 2020

(54) BIOCOMPATIBLE BIODEGRADABLE INTRAOCULAR IMPLANT SYSTEM

(71) Applicant: InSight Innovations, LLC, Littleton, CO (US)

(72) Inventor: Kevin H. Cuevas, Littleton, CO (US)

(73) Assignee: INSIGHT INNOVATIONS, LLC, Littleton, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/268,861

(22) Filed: Sep. 19, 2016

(65) Prior Publication Data

US 2017/0000644 A1 Jan. 5, 2017

Related U.S. Application Data

(63) Continuation of application No. 12/998,652, filed as application No. PCT/US2009/006195 on Nov. 19, 2009, now abandoned.
(Continued)

(51) Int. Cl.
*A61F 2/14* (2006.01)
*A61L 9/00* (2006.01)
(Continued)

(52) U.S. Cl.
CPC .............. *A61F 9/0017* (2013.01); *A61F 2/15* (2015.04); *A61F 2/1602* (2013.01);
(Continued)

(58) Field of Classification Search
CPC .............. A61K 9/0051; A61K 2800/56; A61K 2800/57; A61K 2800/71; A61K 2800/70;
(Continued)

(56) References Cited

U.S. PATENT DOCUMENTS

| 3,794,414 A | 2/1974 | Wesley |
| 3,960,150 A | 6/1976 | Hussain et al. |

(Continued)

FOREIGN PATENT DOCUMENTS

| EP | 0732090 A1 | 9/1996 |
| EP | 1402851 | 3/2004 |

(Continued)

OTHER PUBLICATIONS

Extended European Search Report; EP Application No. 16186404.6; dated Dec. 22, 2016; 7 pages.
(Continued)

*Primary Examiner* — Paul B Prebilic
(74) *Attorney, Agent, or Firm* — Cantor Colburn LLP (57) ABSTRACT

Generally, an intraocular implant and methods for treating an ocular condition. As to certain embodiments, an intraocular biocompatible biodegradable implant (11) which can provide a biocompatible biodegradable material in the form of a flexible membrane (12) containing an active agent (24) which implanted between an intraocular lens (8) and the surface of the posterior capsule (5) of the eye (1)(4) inhibits migration of residual lens epithelial cells after cataract surgery by providing structural or pharmaceutical barriers to reduce posterior capsule (5) opacification of the eye (1)(4).

16 Claims, 7 Drawing Sheets

Related U.S. Application Data (60) Provisional application No. 61/270,567, filed on Jul. 10, 2009, provisional application No. 61/199,674, filed on Nov. 20, 2008.

(51) Int. Cl.

| | | |
|---|---|---|
| *A61F 9/00* | (2006.01) | |
| *A61L 27/54* | (2006.01) | |
| *A61L 27/58* | (2006.01) | |
| *A61K 9/00* | (2006.01) | |
| *A61F 2/16* | (2006.01) | |
| *A61F 2/00* | (2006.01) | |

(52) U.S. Cl.
CPC ............ *A61K 9/0051* (2013.01); *A61L 27/54* (2013.01); *A61L 27/58* (2013.01); *A61F 2002/009* (2013.01); *A61F 2210/0004* (2013.01); *A61F 2230/0065* (2013.01); *A61L 2300/604* (2013.01); *A61L 2300/61* (2013.01); *A61L 2430/16* (2013.01)

(58) Field of Classification Search
CPC ........ A61F 9/0017; A61F 2/15; A61F 2/1601; A61F 2/16015; A61F 2/1613; A61F 2/1694; A61F 2002/1689; A61F 2002/169; A61F 2002/16901; A61F 2002/1699; A61F 2210/0004; A61F 2210/0076; A61F 2230/0065; A61F 2250/003; A61F 2250/0051; A61F 2250/0053; A61F 2250/0063; A61F 2250/0067

See application file for complete search history.

(56) References Cited

U.S. PATENT DOCUMENTS

| | | |
|---|---|---|
| 4,014,335 A | 3/1977 | Arnold |
| 4,124,905 A | 11/1978 | Clark |
| 4,179,497 A | 12/1979 | Cohen et al. |
| 4,441,217 A | 4/1984 | Cozean, Jr. |
| 4,624,669 A | 11/1986 | Grendahl |
| 4,713,072 A | 12/1987 | Bowald |
| 4,772,419 A | 9/1988 | Malson et al. |
| 4,808,181 A | 2/1989 | Kelman |
| 4,865,601 A | 9/1989 | Caldwell et al. |
| 5,098,443 A | 3/1992 | Parel et al. |
| 5,275,624 A | 1/1994 | Hara et al. |
| 5,282,851 A | 2/1994 | Jacob-Labarre |
| 5,354,331 A | 10/1994 | Schachar |
| 5,370,687 A | 12/1994 | Paler |
| 5,405,285 A | 4/1995 | Hirano et al. |
| 5,405,385 A | 4/1995 | Heimke et al. |
| 5,443,505 A | 8/1995 | Wong et al. |
| 5,501,856 A | 3/1996 | Ohroti et al. |
| 5,549,670 A | 8/1996 | Young et al. |
| 5,593,438 A | 1/1997 | Akhavi et al. |
| 5,618,553 A | 4/1997 | Kelleher |
| 5,626,863 A | 5/1997 | Hubbell et al. |
| 5,628,795 A | 5/1997 | Langerman |
| 5,800,533 A | 9/1998 | Eggleston et al. |
| 6,063,116 A | 5/2000 | Kelleher |
| 6,063,396 A | 5/2000 | Kelleher |
| 6,399,693 B1 | 6/2002 | Brennan et al. |
| 6,485,516 B2 | 11/2002 | Boehm |
| 6,524,340 B2 | 2/2003 | Israel |
| 6,551,354 B1 | 4/2003 | Ghazizadeh et al. |
| 6,554,424 B1 | 4/2003 | Miller et al. |
| 6,616,691 B1 | 9/2003 | Tran |
| 6,667,368 B1 | 12/2003 | Brennan et al. |
| 6,713,081 B2 | 3/2004 | Robinson et al. |
| 6,749,634 B2 | 6/2004 | Hanna |
| 6,797,004 B1 | 9/2004 | Brady et al. |
| 6,884,263 B2 | 4/2005 | Valyunin et al. |
| 6,932,839 B1 | 8/2005 | Kamerling et al. |
| 6,972,033 B2 | 12/2005 | McNicholas |
| 7,025,783 B2 | 4/2006 | Brady et al. |
| 7,037,337 B2 | 5/2006 | Carriazo |
| 7,117,807 B2 | 10/2006 | Bohn et al. |
| 7,143,709 B2 | 12/2006 | Brennan et al. |
| 7,169,853 B2 | 1/2007 | Brennan et al. |
| 7,347,970 B2 | 3/2008 | Kim et al. |
| 7,435,258 B2 | 10/2008 | Blake |
| 7,491,350 B2 | 2/2009 | Silvestrini |
| 7,650,848 B2 | 1/2010 | Brennan et al. |
| 7,806,929 B2 | 10/2010 | Brown |
| 8,012,204 B2 | 9/2011 | Weinschenk, III et al. |
| 8,287,592 B2 | 10/2012 | Silvestrini |
| 8,303,655 B2 | 11/2012 | Basoglu et al. |
| 8,308,800 B2 | 11/2012 | Chu |
| 8,551,167 B2* | 10/2013 | Cuevas ..................... A61F 2/14 623/6.16 |
| 8,858,624 B2 | 10/2014 | Christie et al. |
| 9,622,857 B2 | 4/2017 | Coroneo |
| 9,943,404 B2* | 4/2018 | Cuevas ............... A61L 27/3869 |
| 10,028,824 B2* | 7/2018 | Kahook ................ A61F 2/1648 |
| 2001/0034552 A1 | 10/2001 | Young et al. |
| 2002/0010510 A1 | 1/2002 | Silvestrini |
| 2002/0128710 A1 | 9/2002 | Eggleston |
| 2003/0135272 A1* | 7/2003 | Brady ....................... A61F 2/16 623/6.37 |
| 2003/0144733 A1 | 7/2003 | Brady et al. |
| 2003/0149479 A1 | 8/2003 | Snyder et al. |
| 2004/0042073 A1 | 3/2004 | Pynson |
| 2004/0127984 A1 | 7/2004 | Paul et al. |
| 2004/0162612 A1 | 8/2004 | Portney et al. |
| 2004/0236423 A1 | 11/2004 | Zhang et al. |
| 2004/0243231 A1 | 12/2004 | Koziol |
| 2005/0033420 A1 | 2/2005 | Christie et al. |
| 2006/0064161 A1 | 3/2006 | Blake |
| 2006/0100704 A1 | 5/2006 | Blake et al. |
| 2006/0235514 A1 | 10/2006 | Silvestrini |
| 2006/0235515 A1 | 10/2006 | Chassain |
| 2007/0083260 A1 | 4/2007 | Colvard |
| 2007/0106381 A1 | 5/2007 | Blake |
| 2008/0077238 A1 | 3/2008 | Deacon et al. |
| 2008/0077239 A1 | 3/2008 | Zickler et al. |
| 2008/0241223 A1 | 10/2008 | Nivaggioli et al. |
| 2009/0234448 A1 | 9/2009 | Weeber et al. |
| 2010/0126404 A1 | 5/2010 | Brennan et al. |
| 2010/0204788 A1 | 8/2010 | Van Noy |
| 2010/0226943 A1 | 9/2010 | Brennan et al. |
| 2011/0040376 A1 | 2/2011 | Christie et al. |
| 2011/0098808 A1 | 4/2011 | Kobayashi et al. |
| 2011/0230963 A1 | 9/2011 | Cuevas |
| 2011/0295367 A1 | 12/2011 | Cuevas |
| 2011/0313521 A1 | 12/2011 | Angelopoulos |
| 2012/0058302 A1 | 3/2012 | Eggenspieler et al. |
| 2012/0232649 A1 | 9/2012 | Cuevas |
| 2013/0053953 A1 | 2/2013 | Silvestrini |
| 2013/0053954 A1 | 2/2013 | Rao et al. |
| 2013/0153612 A1 | 6/2013 | O'Brien et al. |
| 2013/0304205 A1 | 11/2013 | Cuevas |
| 2016/0074154 A1 | 3/2016 | Woods |

FOREIGN PATENT DOCUMENTS

| | | |
|---|---|---|
| EP | 2305178 | 4/2011 |
| FR | 2 832 920 A1 | 6/2003 |
| WO | 9208422 A1 | 5/1992 |
| WO | WO 93/09732 | 5/1993 |
| WO | 2008036674 A1 | 3/2008 |
| WO | WO 2008/108523 | 9/2008 |
| WO | WO 2010/059214 | 5/2010 |
| WO | 2016022933 A1 | 2/2016 |

OTHER PUBLICATIONS

U.S. Appl. No. 14/298,318, filed Jun. 6, 2014.
U.S. Appl. No. 62/034,401, filed Aug. 7, 2014.
U.S. Appl. No. 61/199,674, filed Nov. 20, 2008.
U.S. Appl. No. 61/270,567, filed Jul. 10, 2009.

(56) References Cited

OTHER PUBLICATIONS

International Patent Cooperation Treaty Patent Application No. PCT/US2009/006195, filed Nov. 19, 2009.
International Patent Cooperation Treaty Patent Application No. PCT/US2012/049176, filed Aug. 1, 2012.
International Patent Cooperation Treaty Patent Application No. PCT/US2013/041574, filed May 17, 2013.
Cleary et al.Effect of Square-edged Intraocular Lenses on Neodymium:YAG Laser Capsulotomy Rates in the United States.J. Cataract&Refractive Surgery,vol. 13,Nov. 2007,p. 1899-1906.
Cortina et al. Diclofenac Sodium and Cyclosporine A Inhibit Human Lens Epithelial Cell Proliferation in Culture.Graefes Arch Clin Exp Ophthalmol,vol. 235,Mar. 1997,pp. 180-185.
Emery. Capsular Opacification After Cataract Surgery. Curr Opin in Ophthalmol, vol. 10, 1999, pp. 73-80.
Hara et al.Long-Term Study of Posterior Capsular Opacification Prevention With Endocapsular Equator Rings in Humans. Arch Ophthalmol,Jul. 2011, vol. 129(7), pp. 855-863.
Hartmann et al. Prevention of Secondary Cataract by Intracapsular Administration of the Antibiotic Daunomycin. Ophthalmol, vol. 4, Jan. 1990, pp. 102-106. (abstract only).
Inan et al. Effect of Diclofenac on Prevention of Posterior Capsule Opacification in Human Eyes. Can J Ophthalmol, vol. 41, Oct. 2006, pp. 624-629.
Inan et al. Prevention of Posterior Capsule Opacification by Retinoic Acid and Mitomycin. Graefes Arch Clin Exp Ophthalmol, vol. 239, Aug. 2001, pp. 693-697.
Inan et al. Prevention of Posterior Capsule Opacification by Intraoperative Single-dose Pharmacologic Agents. J Cataract Refract Surg, Jul. 2001, vol. 27, pp. 1079-1087.
Ismail et al. Prevention of Secondary Cataract by Antimitotic Drugs: Experimental Study. Ophthalmic Res, 1996, vol. 28(1), pp. 64-69.
Kavoussi, et al. Prevention of Capsular Bag Opacification with a New Hydrophilic Acrylic Disk-Shaped Intraocular Lens.J Cataract Refract Surg, Dec. 2011, 37, pp. 2194-2200.
Maloof et al. Selective and Specific Targeting of Lens Epithelial Cells During Cataract Surgery Using Sealed-Capsule Irrigation. J Cataract Refract Surg, Aug. 2003, vol. 29, pp. 1566-1568.
Oberleithner et al. Fusion of renal epithelial cells: A model of studying cellular mechanisms of ion transport. Proc. Natl. Acad. Sci. USA, May 1986, vol. 83, pp. 3547-3551.
Osnsupersite. New Accommodating IOL Offers High Rate of Spectacle Independence; Website, http://www.osnsupersite.com, originally downloaded Apr. 4, 2012, 3 total pages.
Melki et al. An implantable intraocular pressure transducer: Initial safety outcomes. JAMA Ophthalmology, Oct. 2014, vol. 132, No. 10, pp. 1221-1225.
Tekia. Website, http://tekia.com, originally downloaded Apr. 4, 2012, 1 page.
U.S. Appl. No. 12/998,652; Office Action dated Aug. 7, 2012.
U.S. Appl. No. 12/998,652; Office Action dated Aug. 27, 2012.
U.S. Appl. No. 12/998,652; Office Action dated Mar. 18, 2013.
U.S. Appl. No. 13/136,515; Office Action dated Dec. 17, 2012.
U.S. Appl. No. 13/136,515; Office Action dated Feb. 13, 2013.
Corresponding European patent application No. 09827868.2; Office Action dated Mar. 6, 2013, 7 total pages.
Bluestein, et al. Dimensions of the Pediatric Crystalline Lens: Implications for Intraocular Lenses in Children. J Pediatr Ophthalmol Strabismus, Jan.-Feb. 1996, 33(1), pp. 18-20.
Menlyweb. Andre "the Giant" Roussimoff. Website, http://www.manlyweb.com, Dec. 2007, 3 total pages.
Noardi. Eye Size Chart. Website, http://www.noardi.net, Aug. 2013, 4 total pages.
Roarty, et al. Normal pupil size and anisocoria in newborn infants. Arch Ophthalmol, Jan. 1990, 108(1):94-95.
Leishman et al. Prevention of capsular bag opacification with a modified hydrophilic acrylic disk-shaped intraocular lens. J Cataract Refract Surg,Sep. 2012,38:1664-1670.
Werner et al. Experimental evaluation of ophthalmic devices and solutions using rabbit models. Veterinary Ophthalmology, Sep. 2006, 9, 5, pp. 281-291.
European Patent Application No. 12820279.3; Office Action dated Jan. 27, 2015, 10 total pages.
Corresponding EP Patent Application No. 09827868.2; Response to Office Action filed Feb. 24, 2014, 17 total pages.
PCT International Patent Application No. PCT/US2015/044357; International Search Report and Written Opinion of the International Search Authority dated Feb. 1, 2016.
Kirschner et al. Microtopographies Inhibit Human Lens Epithelial Cell Migration in Posterior Capsule Opacification Model. 2014 Annual Meeting of Biomedical Engineering Society, Oct. 2014, San Antonio, 1 page total.
Magin et al. Micropatterned Protective Membranes Inhibit Lens Epithelial Cell Migration in Posterior Capsule Opacification Model. Translational Vision Science & Technology, Mar. 2015, 4(2):9, 8 pages total.

* cited by examiner

BIOCOMPATIBLE BIODEGRADABLE INTRAOCULAR IMPLANT SYSTEM

This United States Patent Application is a continuation of currently abandoned U.S. patent application Ser. No. 12/998,652, filed May 13, 2011, which is a United States National Stage of International Patent Cooperation Treaty Patent Application No. PCT/US2009/006195, filed Nov. 19, 2009, which claims the benefit of U.S. Provisional Patent Application 61/270,567, filed Jul. 10, 2009 and U.S. Provisional Patent Application No. 61/199,674, filed Nov. 20, 2008, each hereby incorporated by reference herein.

I. TECHNICAL FIELD

Generally, an invention comprising an intraocular implant and methods for treating an ocular condition. In particular, an embodiment of an intraocular biocompatible biodegradable implant including a biocompatible biodegradable material and an active agent which implanted between an intraocular lens and the surface of the posterior capsule of the eye inhibits migration of residual lens epithelial cells after cataract surgery by providing structural or pharmaceutical barriers to reduce posterior capsule opacification of the eye.

II. BACKGROUND

Visually impairing cataract is the leading cause of preventable blindness in the world. Presently, the only known treatment for cataract is the surgical removal of the opacified lens of the affected eye and replacement with an artificial intraocular lens ("IOL"). Technological advances in cataract surgery with IOL implantation have made cataract surgery among the most effective surgical procedures.

Figure 1:
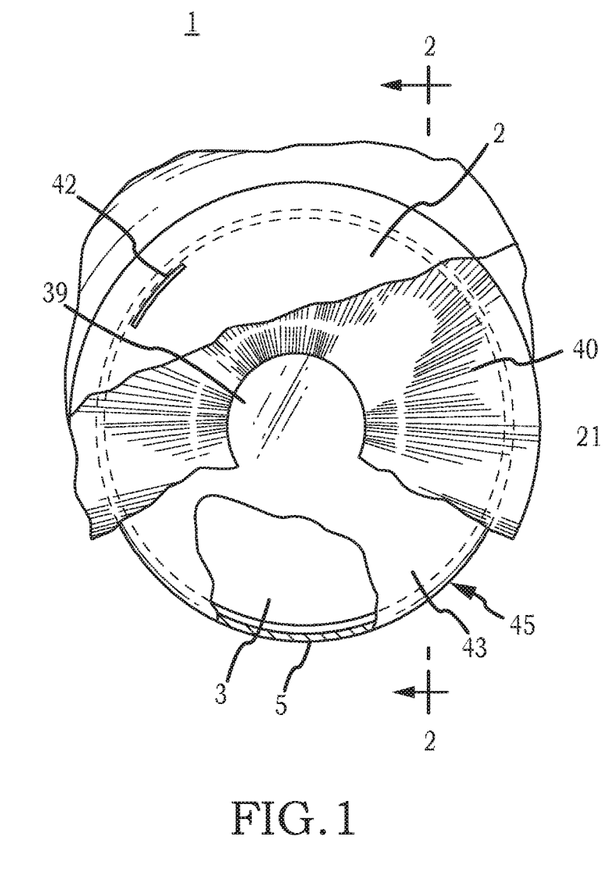
FIG. 1 is a top view of the phakic eye with the natural lens intact.
Figure 2:
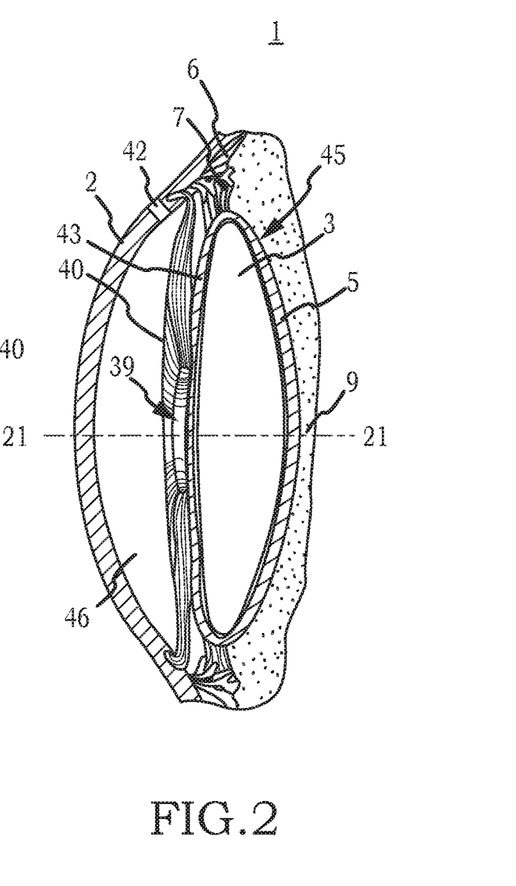
FIG. 2 is a cross section 2-2 of the phakic eye with the natural lens intact.
Figure 3:
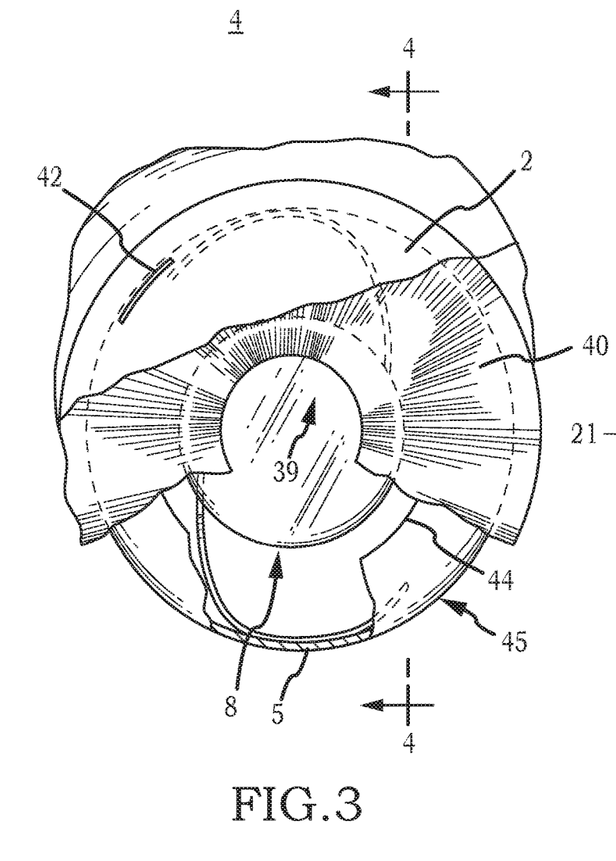
FIG. 3 is a top view of the pseudophakic eye having the natural lens replaced with an IOL.
Figure 4:
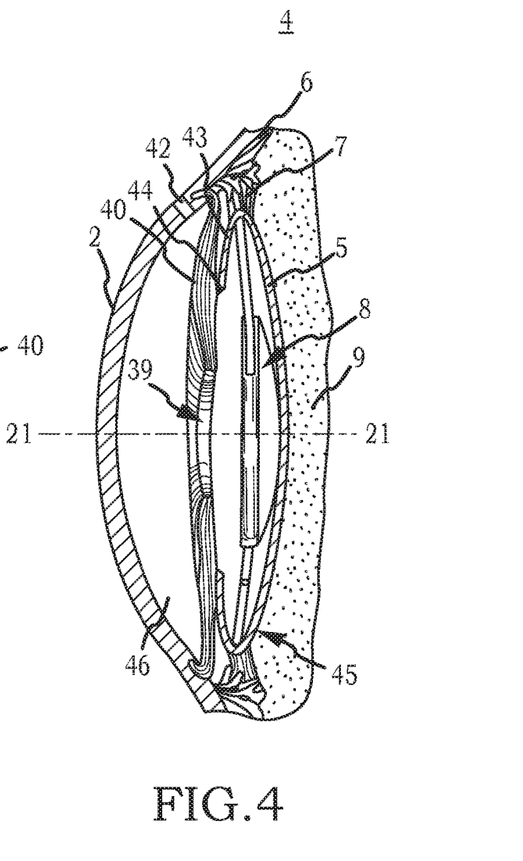
FIG. 4 is a cross section 3-3 of the psuedophakic eye having the natural lens replaced with an IOL.
Figure 5:
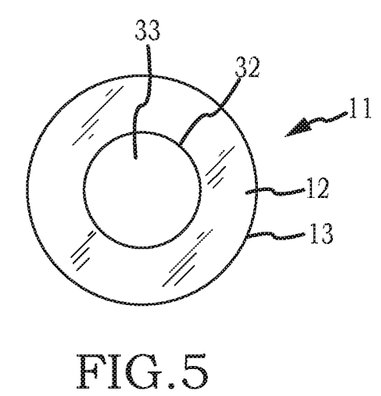
FIG. 5 is a front view of a particular embodiment of the inventive intraocular implant of generally circular configuration.

Now referring primarily to FIGS. 1 and 2, which show a top view and a cross section view of a phakic eye (1). The most common technique of cataract surgery may be extracapsular cataract extraction ("ECCE") which involves the creation of an incision (42) near the outer edge of the cornea (2) and a circular opening (44)(shown in FIGS. 3 and 4) in the anterior lens capsule (43)(also herein referred to as the "anterior capsule") through which the opacified lens (3) can be removed from the lens capsule (45)(also referred to as the "capsular bag"). Now referring primarily to FIGS. 3 and 4 which show a top view and a cross section view of a psuedophakic eye (4), the lens capsule (43) anchored to the ciliary body (6) through the zonular fibers (7) can be left substantially intact. The IOL (8) can then be placed within the lens capsule (43) through the circular opening (44) in the anterior capsule (43). The IOL (8) can be acted on by zonular forces exerted on the outer circumference of the lens capsule (45) which establishes the location of the IOL (8) within the lens capsule (45). The intact posterior capsule (5) acts as a barrier to the vitreous humor (9) within the posterior segment of the eye.

The most frequent complication to ECCE and other methods of cataract surgery can be opacification of the posterior capsule (5). Posterior capsule opacification ("PCO") results from the migration of residual lens epithelial cells ("LEC") between the IOL (8) and the surface of the posterior capsule (5) subsequent to cataract surgery. The residual LECs once located between the IOL (8) and the surface of the posterior capsule (5) can proliferate leading to clouding of the normally clear posterior capsule (5). Clouding of the posterior capsule (5) can decrease visual acuity if the opacification occurs within the visual axis (21).

Visually significant PCO requires an additional surgery to clear the visual axis of the eye. Presently, the most widely utilized procedure to clear the visual axis of PCO may be Neodymium: Yttrium-Aluminum-Garnet ("Nd:YAG") laser capsulotomy. However, there may be substantial problems with this procedure such as IOL damage, postoperative intraocular pressure spikes, vitreous floaters, cystoid macular edema, retinal detachment, and IOL subluxation, or the like. Additionally, pediatric patients can be difficult to treat and a delay in treatment can lead to irreversible amblyopia. Many underdeveloped countries do not have access to a Nd:YAG laser and the cost can be prohibitive.

Prevention or inhibition of PCO fall into two broad categories: mechanical and pharmacological. Mechanical mechanisms to inhibit PCO have primarily focused on configuration of the IOL (8). Configuring the IOL to include a sharp posterior edge may provide a structural barrier to the migration of residual LECs between the IOL and the surface of the posterior capsule (5). Cleary et al., *Effect of Square-edged Intraocular Lenses on Neodymium: YAG Laser Capsulotomy Rates in the United States*, J. Cataract & Refractive Surgery, Vol. 13, p. 1899 (November 2007). However, while introduction of square edged IOLs appears to have reduced incidence of PCO, a review of Medicare claims data from 1993 to 2003 evidences that the number of laser capsulotomies performed in the United States to treat PCO in recipients of square edged IOL remains substantial.

Pharmacological mechanisms have been proposed as a way to inhibit or prevent PCO. The effect of topical treatment with nonsteroidal anti-inflammatory drugs ("NSAIDs") such as diclofenac and indomethacin after phacoemulsification do not appear to inhibit PCO. Inan et al., *Effect of Diclofenac on Prevention of Posterior Capsule Opacification in Human Eyes*, Can J Ophthalmol, 41; 624-629 (2006). Additionally, the majority of pharmacological agents tested in vitro for inhibition of migration and proliferation of LECs are antimetabolites and antimitotics which have not been used clinically because of their toxic side effects. Inan U U, Ozturk F, Kaynak S, et al. *Prevention of Posterior Capsule Opacification by Intraoperative Single-dose Pharmacologic Agents*, J Cataract Refract Surg, 27:1079-87 (2001); Inan U U, Ozturk F, Kaynak S. Ilker S S, Ozer E, Güler, *Prevention of Posterior Capsule Opacification by Retinoic Acid and Mitomycin*, Graefes Arch Clin Exp Ophthalmol 239: 693-7 (2001); Cortina P, Gomez-Lechon M J Navea A, Menezo J L, Terencio M C, Diaz-Llopis, M, *Diclofenac Sodium and Cyclosporine A Inhibit Human Lens Epithelial Cell Proliferation in Culture*, Graefes Arch Clin Exp Ophthalmol 235:180-5 (1997); Ismail M M, Alio J L, Ruiz Moreno J M, *Prevention of Secondary Cataract by Antimitotic Drugs: Experimental Study*, Ophthalmic Res, 28:64-9 (1996); Emery J., *Capsular Opacification After Cataract Surgery*, Curr Opin Ophthalmol 9:60-5 (1999); Hartmann C, Wiedemann P, Gothe K, Weller M, Heimann K, *Prevention of Secondary Cataract by Intracapsular Administration of the Antibiotic Daunomycin*, Ophthalmologic, 4:102-6 (1990).

Also, available is a sealed capsule irrigation device which functions to allow selective irrigation of the lens capsule with LEC inhibiting pharmacologic agents. Maloof A J, Neilson G, Milverton E J, Pandy S K, *Selective and specific targeting of lens epithelial cells during cataract surgery using sealed-capsule irrigation*, J Cataract Refract Surg, 29:1566-68 (2003). It is not clear, however, that use of the device can be reduced to routine practice. Problems relating to incomplete seal of the lens capsule (45) resulting in leakage of potentially toxic chemicals into the anterior chamber (46) of the eye, rupture of the lens capsule (45) during manipulation of the irrigation device, difficulty in assessing kill of LECs within the lens capsule and an increase in the duration of routine cataract surgery limit the usefulness of the irrigation device.

Another prominent problem with routine cataract surgery and other surgical procedures such as retinal surgery, cornea transplant surgery, glaucoma surgery, or the like, can be postoperative administration of antibiotics to prevent endophthalmitis. Topical antibiotic and anti-inflammatory eye drops represent the mainstay of drug delivery for intraocular surgery.

However, there has yet to be a prospective randomized study showing that topical antibiotics prevent endophthalmitis. Also, because the human cornea acts as a natural barrier to biologic and chemical insults, intraocular bioavailability usually requires frequent dosing regimens for each medication. Topical drops can be difficult for young and elderly patients and the drop schedule can be cumbersome and confusing particularly when following surgery each eye is on a different drop schedule. These difficulties can result in non-compliance with serious consequences such as endophthalmitis, glaucoma, and cystoid macular edema. Recent prospective studies supporting the use of intracameral antibiotic injections for prophylaxis of endophthalmitis have stirred debate regarding the risks associated with this method of antibiotic prophylaxis including the short duration of protective effect (possibly less than 24 hours), the introduction of potentially contaminated substances in the anterior chamber, endothelial cell toxicity, toxic anterior segment syndrome, dilutional and osmolarity errors during mixing, and the like. Also, the systemic administration of drugs for treatment of localized ocular conditions may not be preferred because of the inefficiency associated with indirect delivery of the drugs to a target organ.

Recognizing these disadvantages of conventional delivery of antibiotics and other drugs to the eye, external ocular inserts were developed utilizing biologically inert materials to act as a reservoir for slow release of the drug. These external ocular inserts may be placed within the upper and lower conjunctival fornix of the eye to achieve a uniform sustained rate of release of drug in therapeutically effective amounts. However, patients can be intolerant of these devices due to difficulty in insertion and removal and mild to moderate conjunctival irritation during use which may explain why external ocular inserts have not been widely accepted in clinical practice.

III. DISCLOSURE OF INVENTION

Accordingly, a broad object of the invention can be to provide a biocompatible intraocular implant and methods of treatment of an ocular condition by implantation of the biocompatible intraocular implant inside the eye with embodiments which can be intraocularly implanted in the posterior capsule of the eye to provide mechanical or pharmaceutical barriers or both to interrupt progression of the ocular condition, the ciliary sulcus between the iris and the lens, or in the anterior chamber overlaying the iris.

Another broad object of the invention can be to provide a biocompatible intraocular implant locatable between the surface of the posterior capsule of the eye and an implanted IOL to provide a mechanical barrier for treatment of an ocular condition.

Another broad object of the invention can be to provide a biocompatible biodegradable intraocular implant locatable between the surface of the posterior capsule of the eye and an implanted IOL to provide a biodegradable mechanical barrier for treatment of an ocular condition.

Another broad object of the invention can be to provide a biocompatible biodegradable intraocular implant locatable between the surface of the posterior capsule of the eye and an implanted IOL which combines a biocompatible biodegradable material which continually, or substantially continually, releases a therapeutically effective amount of an active agent to treat an ocular condition.

Another broad object of the invention can be to provide a biocompatible biodegradable intraocular implant locatable between the surface of the posterior capsule of the eye and an implanted IOL during cataract surgery which by structural or pharmaceutical barriers inhibits migration of residual lens epithelial cells to the surface of the posterior capsule.

Another broad object of the invention can be to provide a biocompatible biodegradable intraocular implant locatable between the surface of the posterior capsule of the eye and an implanted IOL during cataract surgery which by structural or pharmaceutical barriers inhibits proliferation of residual lens epithelial cells to the surface of the posterior capsule as a prophylaxis of PCO.

Another broad object of the invention can be to provide a biocompatible or biocompatible biodegradable intraocular implant locatable anterior to the natural crystalline lens or an implanted IOL within the ciliary sulcus for administration of one or more active agents.

Another broad object of the invention can be to provide a biocompatible or biocompatible biodegradable intraocular implant locatable in the anterior chamber overlaying the iris.

Naturally, further objects of the invention are disclosed throughout other areas of the specification, drawings, photographs, and claims.

V. MODE(S) FOR CARRYING OUT THE INVENTION

Generally, the invention comprises an intraocular implant and methods for treating an ocular condition. In particular, an embodiment of a biocompatible biodegradable intraocular implant including a biocompatible material or a biocompatible biodegradable material and an active agent which implanted between an IOL and the surface of the posterior capsule of the eye inhibits migration of residual LECs after cataract surgery by providing structural or pharmaceutical barriers to reduce posterior capsule opacification of the eye.

Definitions

"A" or "an" entity refers to one or more of that entity; for example, "a polymer" refers to one or more of those compositions or at least one composition. As such, the terms "a" or "an", "one or more" and "at least one" can be used interchangeably herein. Furthermore, the language "selected from the group consisting of" refers to one or more of the elements in the list that follows, including combinations of two or more of the elements.

"About" for the purposes of the present invention means that ranges may be expressed as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. In the context of such a numerical value or range "about" means plus or minus 10% of the numerical value or range recited or claimed.

"Active agent" for the purposes of this invention means any substance used to treat an ocular condition.

"Biocompatible" for the purposes of this invention means the ability of any material to perform the intended function of an embodiment of the invention without eliciting any undesirable local or systemic effects on the recipient and can include non-biodegradable materials such as: polyurethanes, polyisobutylene, ethylene-alpha-olefin copolymers, acrylic polymers and copolymers, vinyl halide polymers and copolymers, polyvinyl esters, polyvinylidene chloride, polyacrylonitrile, polyvinyl ketones, polyvinyl aromatics such as polystyrene, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyesters, epoxy resins, rayon-triacetate, cellophane, or the like, or biodegradable materials, as herein described.

"Biodegradable" for the purposes of this invention means the ability of any biocompatible material to breakdown within the physiological environment of the eye by one or more physical, chemical, or cellular processes at a rate consistent with providing structural or pharmaceutical barriers (or both) at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly($\varepsilon$-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like. Hydrogels such as methylcellulose which act to release drug through polymer swelling are specifically excluded from the term.

"Intraocular" for the purposes of this invention means inside the eyeball (also referred to as an "eye") and without limitation to the forgoing the anterior chamber, the ciliary sulcus, and posterior capsule of the eye; however, specifically excluding the external surface of the eye or intracorneal or intrasclera regions of the eye.

"Localized Region" for the purposes of this invention means substantially within a localized tissue region of the eye therapeutically affected (whether structurally or pharmaceutically) by implantation of embodiments of an intraocular implant.

"Ocular condition" for the purposes of this invention means a disease, ailment or condition which affects or involves the eye or any one of the parts or regions of the eye, such as PCO. The eye includes the eyeball and the tissues and fluids which constitute the eyeball, the periocular muscles (such as the oblique and rectus muscles) and the portion of the optic nerve which is within or adjacent to the eyeball.

"Posterior ocular condition" for the purposes of this invention means a disease, ailment or condition which affects or involves a posterior ocular region or site such as the choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Suitable for implantation" for the purposes of this invention means with regard to embodiments of the intraocular implant dimensions which allow insertion or implantation without causing excessive tissue damage.

"Therapeutic level" for the purposes of this invention means an amount or a concentration of an active agent that has been locally delivered to an ocular region that is appropriate to reduce, inhibit, or prevent a symptom of an ocular condition.

Now generally referring to FIGS. 5-13, particular embodiments of the inventive intraocular implant (11) can provide a biocompatible flexible membrane or a biocompatible biodegradable flexible membrane (also generally referred to as a "flexible membrane" (12)) having an outer boundary (13) configured to allow the intraocular implant (11) to locate in the concavity of the posterior capsule (5) of the psuedophakic eye (4), or other localized region inside the eye such as the ciliary sulcus or anterior chamber (46) depending on the application. As a non-limiting example, the intraocular implant (11) can be located in the posterior capsule (5) for the purpose of isolating the surface of the posterior capsule (5) from migration of residual LECs after cataract surgery, or reducing or preventing the migration of residual LECs between the surface of an IOL (8) implanted in the lens capsule (45) and the surface of the posterior capsule (5).

Intraocular implants (11) suitable for implantation can provide a flexible membrane (12) having an outer boundary (13) which as a non-limiting example defines a circular area having a diameter in a range of about 9 millimeters ("mm") and about 15 mm depending on the recipient; however, the invention is not so limited, and the outer boundary (13) can define a substantially circular, ovoid, or other configuration of the outer boundary (13) suitable for implantation into the concavity of the posterior capsule (5) of the psuedophakic eye (4), or other localized region inside the eye.

Figure 8:
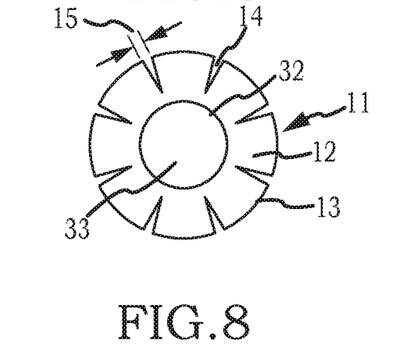
FIG. 8 is a front view of a particular embodiment of the inventive intraocular implant which further provides radial slit elements originating at the outer boundary.

Now referring primarily to FIG. 8, particular embodiments of the flexible membrane (12) can further include one or more radial slit elements (14) cut through the thickness of the flexible membrane with the radial slit elements (14) originating at the outer boundary (13) cut a distance radially toward the center of the flexible membrane (12). The one or more radial slit elements (14) can have sufficient length and width to allow the flexible membrane (12) to conform to a greater extent with the concavity of the posterior capsule (5) of the psuedophakic eye (4) or other localized region inside the eye. As one non-limiting example, the radial slit elements (14) can provide an opening in the flexible membrane (12) having a greater slit width (15) at the outer boundary (13) of the flexible membrane (12) than proximate the center of the flexible membrane (12). As a non-limiting example, the flexible membrane (12) when received by the concavity of the posterior capsule (5) can deform to reduce the slit width (15) at the outer boundary (13) of the flexible membrane (12).

Figure 12:
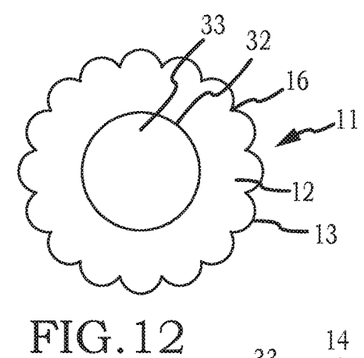
FIG. 12 is a front view of a particular embodiment of the inventive intraocular implant which further provides one or more recess elements.
Figure 13:
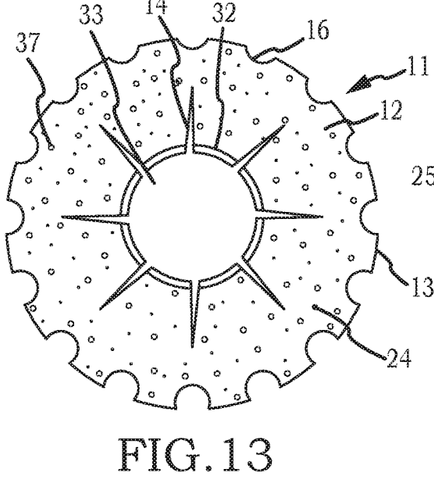
FIG. 13 is a front view of a particular embodiment of the inventive intraocular implant which includes both radial slit element originating from the aperture element and recess elements which periodically interrupt the outer boundary.

Now referring primarily to FIGS. 12 and 13, particular embodiments of the flexible membrane can further provide one or more recess elements (16) located along the outer boundary (13) of the flexible membrane (12). The outer boundary (13) of the flexible membrane (12) can be interrupted once or periodically to provide one or more of the recess elements (16) which can be configured, for example, as semicircular notches, triangular notches, indents, or the like which can function to allow added flexure to more readily locate the flexible membrane in the posterior capsule of the eye (or other localized region), as above described, or can function to reduce sequestration of peripheral cortical material during the final irrigation and aspiration steps in cataract surgery.

Figure 6:
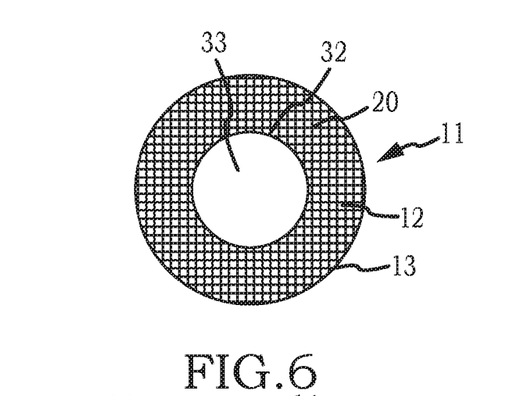
FIG. 6 is a front view of a particular embodiment of the inventive intraocular implant further providing patterned surface elements.
Figure 7:
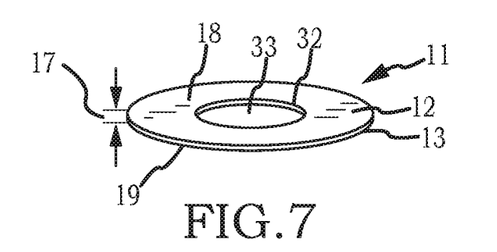
FIG. 7 is a perspective view of particular embodiment of the inventive intraocular implant shown in FIG. 5.

With respect to the particular embodiments of the intraocular implant shown in FIGS. 5-13 and specifically referring to FIG. 7 as a non-limiting example, the flexible membrane (12) can have a thickness (17) disposed between a front surface (18) and a back surface (19)(also referred to as "a first side" and "a second side" or "opposed sides"). As to particular embodiments of the intraocular implant (11), the front surface (18) and the back surface (19) can be disposed in substantially parallel opposed relation providing a relatively uniform thickness of the intraocular implant (11) in a range of about 5 microns ("μm") and about 100 μm. However, certain embodiments of the intraocular implant (11) can provide a flexible membrane (12) thinner proximate the center and thicker proximate the outer boundary (13) or can provide a flexible membrane thicker proximate the center and thinner at the edges depending upon the application. As one non-limiting example, the thickness (17) of the flexible membrane (12) may be thinner in the center to align with the visual axis of the psuedophakic eye (4) to increase visual acuity or promote directional biodegradation of the intraocular implant (11) from the center toward the outer boundary (13).

Figure 21:
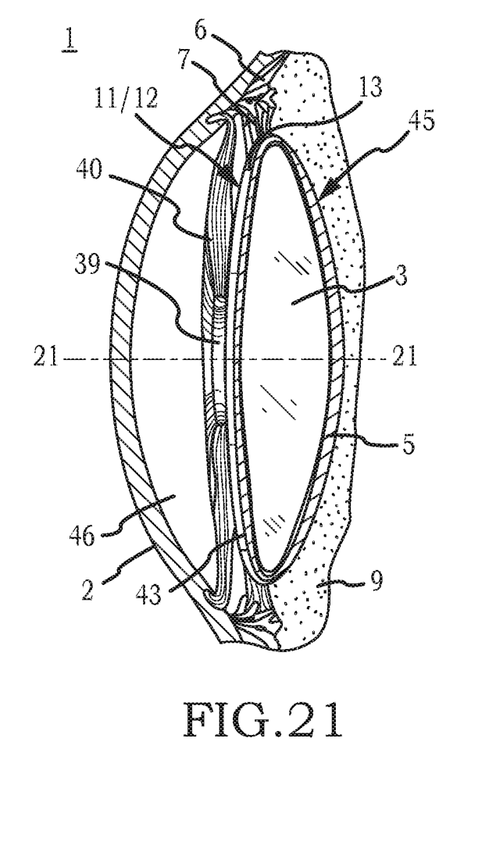
FIG. 21 is a cross section view of the phakic eye having the intraocular implant positioned between the iris and the natural crystalline lens of the eye.

Now referring primarily to FIG. 6, particular embodiments of the intraocular implant (11), can provide patterned surface elements (20) which can engage the surface of the posterior capsule (5) to reduce travel of the intraocular implant (11) or maintain the alignment of the center of the intraocular implant (11) with the visual axis of the eye (21)(see also FIG. 21). The patterned surface elements (20) can provide an irregular or uniform pattern, texture, or roughness sufficient to fix or reduce travel of the intraocular implant (11) in the posterior capsule (5). As to certain embodiments of the intraocular implant (11) the patterned surface elements (20) can also provide pockets which function to provide a localized space to deliver or sequester an amount of an active agent (24). The patterned surface elements can be variously configured to deliver or sequester an active agent (24) depending on the application. The pattern surface elements (20) can be one piece with the flexible membrane (12) or can be applied to the flexible membrane (12) as a pattern surface element layer.

Figure 9:
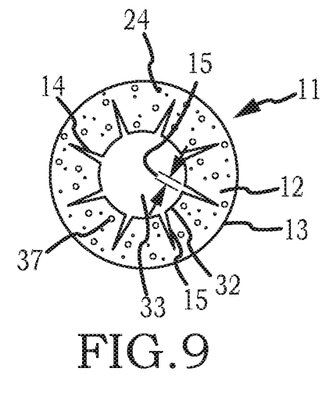
FIG. 9 is a front view of a particular embodiment of the inventive intraocular implant which further provides radial slit elements originating at the aperture element.
Figure 10:
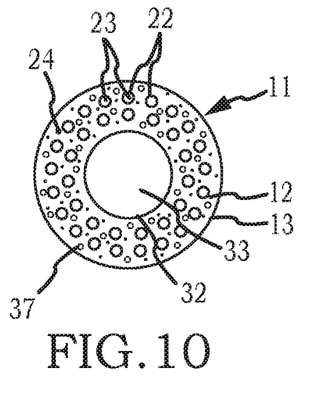
FIG. 10 is a front view of a particular embodiment of the inventive intraocular implant which further provides perforation elements.

Now referring primarily to FIG. 10, certain embodiments of the flexible membrane (12) can further include one or more perforation elements (22) which provide a corresponding one or more perforation openings (23) which communicate between the front surface (18) and the back surface (19) of the flexible membrane (12) for the purpose of increasing rate of biodegradation of the flexible membrane (12) or control release rate of an active agent (24). The active agent (24)(shown for example in FIGS. 9, 10 and 13 as a stipple pattern) is not intended to be limited to those particular embodiments of the intraocular implant (11) or limit the active agent (24) to any particular composition, particle size, or amount.

Figure 14:
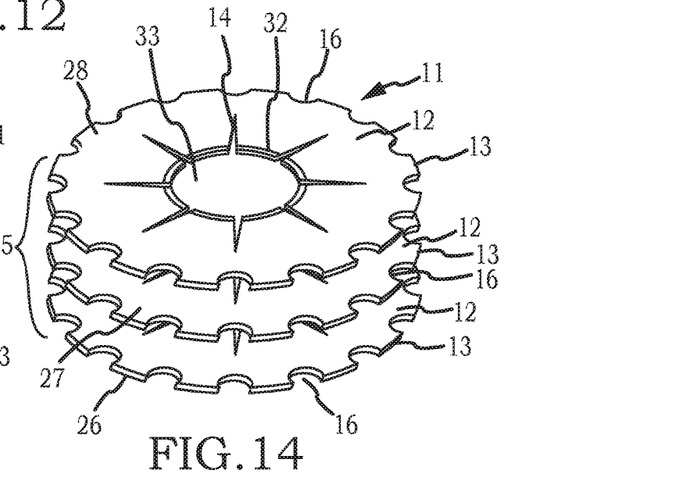
FIG. 14 is a perspective view of a plurality of an embodiment of the inventive intraocular implant which can be stacked front to back.

Now referring primarily to FIG. 14, certain embodiments of the flexible membrane (12) can further provide two or more flexible membrane layers (25). The two or more membrane layers (25) can take the form of a first flexible membrane layer (26) and a second flexible membrane layer (27) or additional flexible membrane layers (28) extruded as a single piece, coupled together as one unit, or stacked front to back (whether single piece, coupled or stacked the term "coupled" may be used to refer to the association of a plurality of flexible membrane layers). Each of the first flexible membrane layer (26) and the second flexible membrane layer (27) or additional flexible layers (28) can be generated from the same or different biocompatible biodegradable materials. As a non-limiting example, in an embodiment of the invention for the treatment of PCO, the first flexible membrane layer (26) can be made of a biocompatible biodegradable material which can have the back surface (19) disposed adjacent the surface of the posterior capsule (5) to provide both a structural barrier to the migration of LECs to the surface of the posterior capsule but to further function as a pharmaceutical barrier which inhibits proliferation or kills LECs by the substantially continuous release of an active agent (24) such as alkylphosphocholine at a rate which provides a therapeutic level, such as a localized concentration of about 1.0 millimolar ("mM") for a period of at least five days to inhibit or prevent PCO. The front surface (18) of the first flexible membrane layer (26) can be coupled adjacent the back surface (19) of the second flexible membrane layer (27) (for example by melt co-extrusion) produced from the same or different biocompatible biodegradable material and the front surface (18) of the second flexible membrane layer (27) can be disposed toward an IOL (8) implanted into the posterior capsule (5) to provide a structural barrier to migration of LECs toward the surface of the posterior capsule and can further function as a pharmaceutical barrier which inhibits proliferation or kills LECs by the substantially continuous release of the same active agent (24) (such as an alkylphosphocholine) or a different active agent (24) such as mitomycin-C at a therapeutic level, such as a localized concentration of about 0.04 mg/mL, for a period of at least about five days to inhibit or prevent PCO. Thus, by configuring the layers in different combinations the rate of release of various active agents can be adjusted depending on the application.

Figure 11:
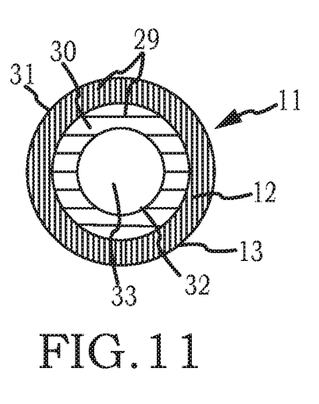
FIG. 11 is a front view of a particular embodiment of the inventive intraocular implant which further provides two more flexible membrane zones.

Now referring primarily to FIG. 11, two or more flexible membrane zones (29) can be established with each flexible membrane zone (29) generated from a particular flexible membrane material. As to certain embodiments, the two or more flexible membrane zones (29) can be established as concentric regions with a first annular zone (30) surrounded by a second annular zone (31). The first annular zone (30) can be of different biocompatible or biocompatible biodegradable material then the second annular zone (31). For example, the first annular zone (30) can provide a biocompatible biodegradable material selected for a greater rate of biodegradation or active agent (24) release (or both) relative to the second annular zone (31) which can provide a biocompatible biodegradable material selected for a lesser rate of biodegradation or active agent (24) release (or both). In that configuration of the inventive intraocular implant (11), the prominent function of the first annular zone (30) can be to provide a pharmaceutical barrier or treatment of an ocular disorder, while the prominent function of the second annular zone (31) can be to provide a structural barrier or treatment of an ocular disorder. In particular embodiments of the inventive intraocular implant for the inhibition of PCO, the first annular zone can be made of the biocompatible biodegradable material poly(lactide-co-glycolide) having an active agent (24) such as alkylphosphocholine dispersed substantially uniformly through out which can provide a pharmaceutical barrier to the proliferation of LECs on the surface of the posterior capsule (5) to inhibit or prevent PCO by release of a therapeutic level of alkylphosphocholine of about 1.0 mM for a period of at least about five days. The first annular zone (30) can substantially biodegrade in the entirety in a period of about five days to about ten days. The second annular zone can be made of the same biocompatible biodegradable material having the same or different active agent (24) dispersed substantially uniformly throughout to provide both a structural barrier to inhibit migration of LECs toward to the surface of the posterior capsule and can provide a pharmaceutical barrier by release of the same or different active agent (24) such as alkylphosphocholine at a therapeutic level or provide a localized concentration of about 1.0 mM for a period of at least twenty days to inhibit or prevent PCO.

Again referring generally to FIGS. 5-16, particular embodiments of the inventive intraocular implant (11) can further include an aperture element (32) having a passage opening (33) sufficiently large to align with the visual axis of the eye (21) to provide a line of sight which passes through the intraocular implant (11) or the first annular zone (30) or the second annular zone (31).

While the aperture element (32) shown in FIGS. 5-14 define a substantially circular passage opening having a diameter in the range of about 1.5 mm and about 9 mm depending upon the application and the recipient; the invention is not so limited and certain embodiments of the inventive intraocular implant (11) can provide an aperture element (32) which defines an oval, square, triangle, or other configuration of passage opening (33) sufficient to provide a line of sight which passes through the intraocular implant (11). As to those embodiments of the invention which are utilized with an intraocular optical implant, such as an IOL as further described herein, the passage opening (33) can be dimensioned in relation to the intraocular optical implant to avoid reduction in the field of vision provided by the intraocular optical implant or to avoid a reduction in clarity of vision within visual field. Alternately, in those embodiments of the invention in which the passage opening (33) has insufficient dimension to avoid overlaying all or part of the visual field afforded by the intraocular optical implant, embodiments of the intraocular implant (11) can be further configured to provide an optical element of sufficient clarity so as not to substantially effect vision within the visual field afforded by an intraocular implant (11).

Now referring specifically to FIGS. 9, 13, and 14, the aperture element (33) can further include one or more radial slit elements (14) each originating at the aperture element (33) and terminating at a distance from the outer boundary (13) of the flexible membrane (12). The one or more radial slit elements (14) can have sufficient length and width to allow the flexible membrane (12) to conform to a greater extent with the concavity of the posterior capsule (5)(or other localized region) of the eye and with respect to embodiments of the intraocular implant (11) which are biodegradable can function to promote directional biodegradation of the intraocular implant proximate the aperture element toward the outer boundary (13). Again, the radial slit elements (14) can provide one or more interruptions in the aperture element (32) which can be of lesser or greater width or length to control the rate at which the flexible membrane (12) biodegrades within the posterior capsule (5) of the eye.

Figure 15:
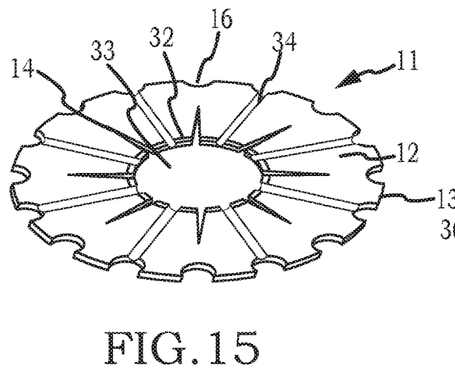
FIG. 15 is a perspective view of an embodiment of the inventive intraocular implant which further provides radial capillary elements.
Figure 16:
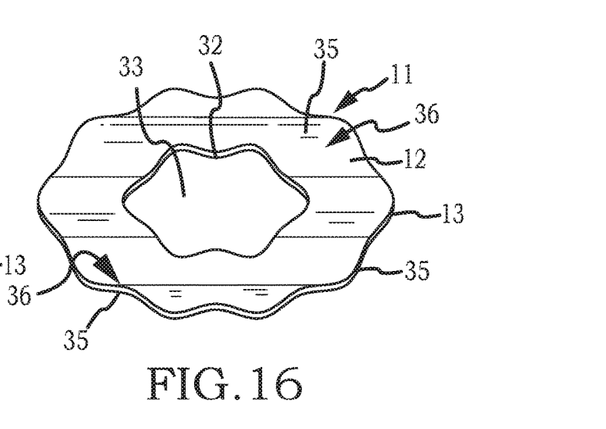
FIG. 16 is a perspective view of an embodiment of the inventive intraocular implant which further provides corrugate elements.

Now referring primarily to FIGS. 15 and 16, particular embodiments of the intraocular implant (11) can further provide radial capillaries (34) which communicate between the outer boundary (13) and the aperture element (32) of the flexible membrane (12) configured to allow or facilitate circulation of the fluid within the eye, for example, between the flexible membrane (12) and the posterior capsule (5) of the eye. Similarly, as shown by FIG. 16, particular embodiments of the intraocular implant (11) can further provide one or more corrugate elements (35) which can be disposed in substantially linear parallel relation to generate undulations in the flexible membrane (12) sufficient when the flexible membrane (12) locates against the surface of the posterior capsule (5)(or surface of a localized region) to provide channels (36) in which the fluids of the eye can circulate.

Referring in general to FIGS. 5-16, embodiments of the intraocular implant can further include an active agent (24)(shown as stipple pattern in FIGS. 9, 10, and 13 although the invention is not so limited) mixed with or dispersed in the biodegradable polymer of the flexible membrane (12). The composition of the biodegradable polymers of the flexible membrane (12) of the intraocular implant (11) can be varied to provide a continuous or substantially continuous release of a therapeutic level of a particular active agent (24) or a particular mixture of active agents (24) effective for the ocular condition being treated. Active agents (24) that can be used include, but are not limited to (either alone or in combination): ace-inhibitors, endogenous cytokines, agents that influence the basement membrane, agents that influence the growth of endothelial or epithelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites such as daunomycin, antiangiogenic agents, tyrosine kinase inhibitors, antibiotics such as aminoglycosides such as gentamicin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline, minocycline, and doxycycline; quinolones such as ciprofloxacin, moxifloxacin, gatifloxacin, and levofloxacin; sulfonamides such as chloramine T; sulfones such as sulfanilic acid; anti-viral drugs such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, ketorolac, naproxen, an anesthetic, lidocaine; beta.-adrenergic blocker or beta.-adrenergic agonist such as ephedrine, and epinephrine; aldose reductase inhibitor such as epalrestat, ponalrestat, sorbinil, tolrestat; antiallergic such as cromolyn, beclomethasone, dexamethasone, and flunisolide; colchicine, anihelminthic agents such as ivermectin and suramin sodium; antiamebic agents such as chloroquine and chlortetracycline; and antifungal agents such as amphotericin; anti-angiogenesis compounds such as anecortave acetate; retinoids such as Tazarotene, anti-glaucoma agents such as brimonidine (Alphagan and Alphagan P), acetozolamide, bimatoprost (Lumigan), timolol, mebefunolol; memantine; alpha-2 adrenergic receptor agonists; 2-methoxyestradiol; anti-neoplastics such as vinblastine, vincristine, interferons; alpha, beta and gamma., antimetabolites such as folic acid analogs, purine analogs, and pyrimidine analogs; immunosuppressants such as azathyprine, cyclosporine and mizoribine; miotic agents, such as carbachol, mydriatic agents such as atropine, etc., protease inhibitors such as aprotinin, camostat, gabexate, vasodilators such as bradykinin, epidermal growth factor, basic fibroblast growth factor, nerve growth factors, steroidal anti-inflammatory agents such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide; vascular endothelial growth factor inhibitors such as bevacizumab, ranibisumab, pegatanib; transforming growth factor inhibitors; fibroblast growth factor inhibitors, and any of their derivatives.

As to particular embodiments of the inventive intraocular implant the active agent (24) can be dispersed throughout the biocompatible biodegradable polymer of the flexible membrane (12) by mixing the active agent (24) into the melted biodegradable polymer and then solidifying the resulting biodegradable polymer by cooling, having the active agent (24) substantially uniformly dispersed throughout. The biodegradable polymer or mixture of biodegradable polymers can be selected to have a melting point that is below the temperature at which the active agent (24) becomes reactive or degrades. Alternatively, the active agent (24) can be dispersed throughout the biodegradable polymer by solvent casting, in which the biodegradable polymer is dissolved in a solvent, and the active agent (24) dissolved or dispersed in the solution. The solvent is then evaporated, leaving the active agent (24) in the polymeric matrix of the biodegradable material. Solvent casting requires that the biodegradable polymer be soluble in organic solvents. Alternatively, the biodegradable intraocular implant (11) can be placed in a solvent having a concentration of the active agent (24) dissolved and in which the biodegradable intraocular implant swells. Swelling of the biodegradable intraocular implant draws in an amount of the active agent (24). The solvent can then be evaporated leaving the active agent (24) within the flexible membrane (12) of the biodegradable intraocular implant (12). As to each method of dispersing the active agent (24) through out the biodegradable polymer of the flexible membrane (12), therapeutic levels of active agent (24) can be included in biocompatible biodegradable polymer to treat a particular ocular condition. The biodegradable polymer usually comprises at least about 10, at least about 20, at least about 30, at least about 40, at least about 50, at least about 60, at least about 70, at least about 80, or at least about 90 weight percent of the implant with the balance of the weight being the active agent (24) or other non-active agents (37) dispersed in the biocompatible biodegradable polymer (shown as open stipples in FIGS. 9 and 13; however, the non-active agents are not limited to these particular embodiments of the flexible membrane (12)).

Other non-active agents (37) may be included in the biocompatible biodegradable polymer formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

A non-limiting example of producing biodegradable embodiments the inventive intraocular implant for treating an ocular condition such as PCO can be made by mixing an active agent (24) and biodegradable polymer to form an active agent polymer material. The active agent polymer material can be extruded or molded to form embodiments of the biocompatible biodegradable intraocular implant (11) or flexible membrane (12) having active agent release characteristics at a therapeutic level. As but one non-limiting example, the intraocular implant (11) can substantially continuously release active agent (24) to provide a localized concentration of alkylphosphocholine at therapeutic levels of about 0.5 mM to 1.5 mM for at least 5 days or release mitomycin-C to provide a localized concentration of 0.04 mg/mL, or both, for a period of at least about five days to inhibit or prevent PCO. It is to be understood that this specific example of providing an embodiment of an intraocular implant (11) for the inhibition or prevention of PCO, is not intended to be limiting, and embodiments of the intraocular implant (11) can be utilized to treat a wide range of ocular conditions including posterior ocular conditions or anterior chamber conditions of the eye.

Embodiments of the biocompatible flexible membrane (12) or the biocompatible biodegradable flexible membrane (12) can be made by a variety of methods, and while not particularly limited, examples of molding methods which can be used to form a film or sheet includes T-die molding, inflation molding, calender molding, heat press molding, spin cast molding, injection molding, cast molding, or the like.

The inventive intraocular implant (11) of a biodegradable polymer of the invention can be molded in thinner thickness in order to increase biodegradability, but its thickness can be freely adjusted to satisfy strength, flexibility and release of active agent(s) (24) to achieve therapeutically effective levels localized to the site of implantation of the intraocular implant. Thickness of the flexible membrane can be in the range of about 5 µm to about 300 µm, or about 10 µm to 100 µm. Elastic modulus of the flexible can generally be 1,200 MPa or less, more preferably 600 MPa or less. Tensile strength can fall in the range of about 10 MPa to 100 MPa, more preferably in a range of 15 MPa to 70 MPa, further more preferably in a range of 20 MPa to 50 MPa.

Again referring primarily to FIGS. 1-4, as above described the most common surgical technique of cataract surgery may be ECCE (although use of the inventive intraocular implant (11) is not limited to cataract surgery or to any particular technique of cataract surgery) which involves the creation of a circular opening (44) in the anterior lens capsule (43) through which the opacified lens (3) can be removed. The remaining portion of the lens capsule (45), anchored to the ciliary body (6) through the zonular fibers (7) can be left intact. The IOL (8) can then be placed within the lens capsule (43). The IOL (8) can be acted on by zonular forces exerted on the outer circumference of the lens capsule (45) which establishes the location of the IOL (8) within the lens capsule (45). The intact posterior capsule (5) acts as a barrier to the vitreous humor (9).

Figures 17, 18, 19:
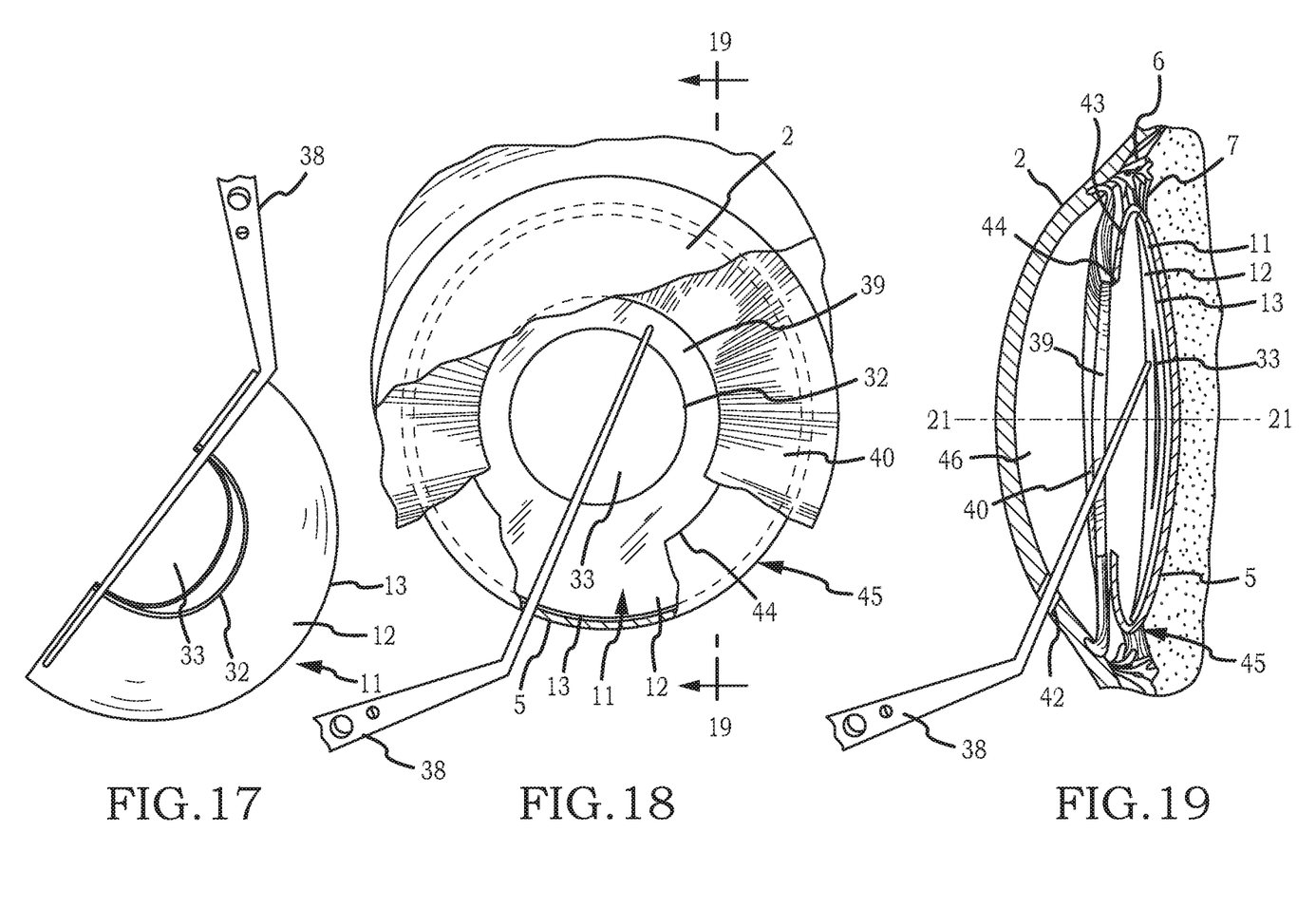
FIG. 17 shows an embodiment of the intraocular implant held by forceps for implantation into an eye having the natural lens removed.
FIG. 18 is top view of the pseudophakic eye having the natural lens removed allowing an embodiment of the intraocular implant to be positioned on the surface the posterior capsule through an opening made in the anterior capsule.
FIG. 19 is a cross section view of the psuedophakic eye having the natural lens removed allowing an embodiment of the intraocular implant to be positioned on the surface the posterior capsule through an incision made in the anterior capsule.

Now referring primarily to FIGS. 17-19, following cataract extraction and cortex removal by ECCE or other surgical procedures to treat other ocular conditions, embodiments of the biocompatible or biocompatible biodegradable intraocular implant (11) can be held in forceps (38) as shown for example in FIG. 17. Embodiments of the intraocular implant (11) may also be removably fixed to the surface of a small card (41) from which it can be lifted with the forceps (38) prior to insertion into the eye as shown for example in FIGS. 22 and 23. The intraocular implant (11) can be folded upon itself to reduce the apparent dimension for passage through the corneal or scleral incision (42) as well as circular opening (44) in the anterior lens capsule (43) surrounded by the pupil (39) of the iris (40), as shown in FIGS. 17-19.

Now referring specifically to FIG. 19, which provides an example of a non-limiting method, the intraocular implant (11) can be positioned within localized region of the lens capsule (45) having a front surface (18)(or first side) proximate the surface of the posterior capsule (5). The passage opening (33), of embodiments of the intraocular implant (11) which provide an aperture element (32), can be aligned with the visual axis of the eye (21) to provide a line of sight which passes through the passage opening (33) of the intraocular implant (11)(or the first annular zone or the second annular zone of the intraocular implant). The IOL (8) can then be located inside the lens capsule (45) by conventional methods to overlay the intraocular implant (11) placed in the cavity of the posterior capsule (5).

Figure 20:
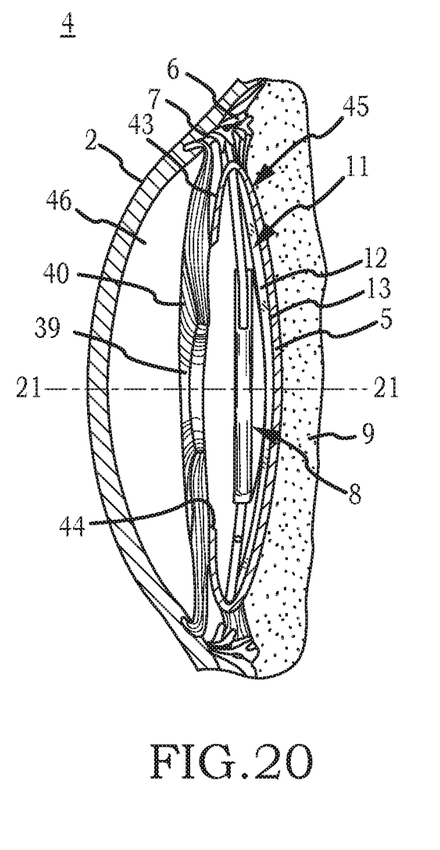
FIG. 20 is a cross section view of the psuedophakic eye having the intraocular implant positioned between the surface the posterior capsule and the implanted IOL.

As a non-limiting example, FIG. 20 shows the IOL (8) overlying the intraocular implant (11) with the passage opening (33) of the aperture element (32) centered underneath the IOL (8). If centration of the intraocular implant (11) is not adequate, it can be readily manipulated into position with a Sinskey Hook or similar instrument. Once implanted into the eye, particular embodiments of the biocompatible biodegradable intraocular implant (12) can biodegrade as above described with normal turnover of the fluid of the eye.

Now referring primarily to FIG. 21, in those surgical procedures in which the natural crystalline lens (3) is not removed such as retinal surgery, cornea transplant surgery, glaucoma surgery, or the like, or in cataract surgery in which the intraocular implant (11) is not located posterior the IOL (8) (for example, due to posterior capsule tear), the intraocular implant (12) can be placed anterior to the natural lens (3) or the IOL (8) within the ciliary sulcus.

Figure 22:
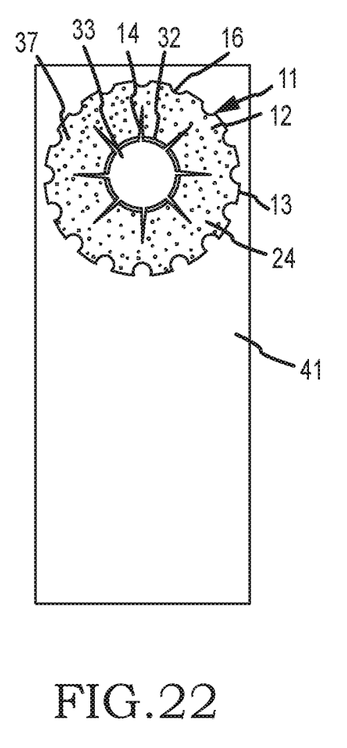
FIG. 22 is front view of an embodiment of the intraocular implant affixed to a sterile card prior to implantation.
Figure 23:
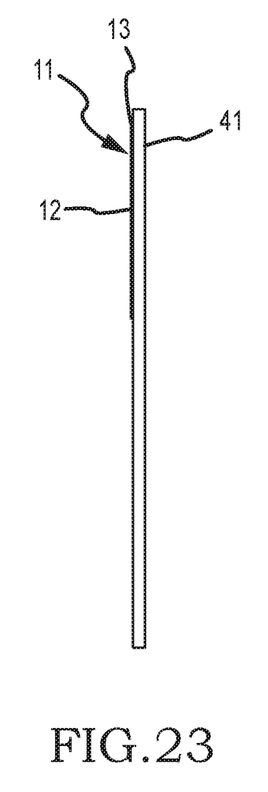
FIG. 23 is a side view of an embodiment of the intraocular implant affixed to a sterile card prior to implantation.

Now referring primarily to FIGS. 22 and 23, the invention can further include a intraocular implant packaging substrate (41) on which embodiments of the inventive intraocular implant (11) can be releasably fixed. The intraocular implant (11) can be removed by manipulation with forceps (38) for use in various applications as above described.

As can be easily understood from the foregoing, the basic concepts of the present invention may be embodied in a variety of ways. The invention involves numerous and varied embodiments of an intraocular implant (11) which as to particular embodiments can be used but is not limited to control of migration of residual lens epithelial cells between the posterior surface of an IOL (8) and the surface of the posterior capsule (5) of the eye to reduce opacification of the posterior capsule (5).

As such, the particular embodiments or elements of the invention disclosed by the description or shown in the figures or tables accompanying this application including the best mode are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an implant" should be understood to encompass disclosure of the act of "implanting"—whether explicitly discussed or not—and, conversely, were there effectively disclosure of the act of "implanting", such a disclosure should be understood to encompass disclosure of "an implant" and even a "means for implanting." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the intraocular implants herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. An intraocular implant, comprising:
   a) a biocompatible flexible membrane implantable between a lens and a surface of a posterior capsule of an eye; wherein the biocompatible flexible membrane has a uniform thickness; wherein said biocompatible flexible membrane is biodegradable and comprises a first flexible membrane layer coupled to a second flexible membrane layer; and
   b) an aperture element which communicates between opposed sides of said biocompatible flexible membrane to provide a passage opening, said passage opening located in said biocompatible flexible membrane to intraocularly align with a visual axis of said eye upon implantation of said biocompatible flexible membrane between said lens and said surface of said posterior capsule of said eye, thereby providing a line of sight which passes through said passage opening; wherein the aperture element defines a circular passage opening having a diameter in the range of about 1.5 millimeter to about 9 millimeters.

2. The intraocular implant of claim 1, further comprising at least one active agent dispersed in said biodegradable biocompatible flexible membrane releasable in sufficient amounts to treat an ocular condition.

3. The intraocular implant of claim 1, wherein said first flexible membrane layer and said second flexible membrane layer comprise different polymeric materials.

4. The intraocular implant of claim 3, wherein said first flexible membrane layer biodegrades at a different rate than said second flexible membrane layer.

5. The intraocular implant of claim 4, wherein at least one of said first flexible membrane layer and said second flexible membrane layer include an active agent.

6. The intraocular implant of claim 5, wherein said first flexible membrane layer and said second flexible membrane layer each contain said active agent, and wherein said active agent contained in said first flexible membrane layer is different than said active agent contained in said second flexible membrane layer.

7. The intraocular implant of claim 1, wherein said biocompatible biodegradable flexible membrane comprises a first annular zone and a second annular zone.

8. The intraocular implant of claim 7, wherein said first annular zone biodegrades at a different rate than said second annular zone.

9. The intraocular implant of claim 8, wherein at least one of said first annular zone and said second annular zone contain an active agent.

10. The intraocular implant of claim 9, wherein said first annular zone and said second annular zone each contain an active agent, and wherein said active agent contained in said first annular zone is different than said active agent contained in said second annular zone.

11. The intraocular implant of claim 1, further comprising an outer boundary of said biodegradable biocompatible flexible membrane which defines a generally circular area.

12. The intraocular implant of claim 11, further comprising a plurality of radial slit elements each originating at said aperture element extending radially outward toward said outer boundary.

13. The intraocular implant of claim 11, further comprising a plurality of radial slit elements each originating at said outer boundary extending radially inward toward said aperture element.

14. The intraocular implant of claim 11, further comprising a plurality of radial capillaries which communicate between said outer boundary and said aperture element, said plurality of radial capillaries configured to allow fluid within said eye to circulate between said first side of said intraocular implant and a surface of said localized region inside said eye.

15. The intraocular implant of claim 11, further comprising a plurality of outer boundary recess elements which periodically interrupt the outer boundary.

16. The intraocular implant of claim 1, further comprising a patterned surface element coupled to said biodegradable biocompatible flexible membrane, said pattern surface element configured to reduce travel of said intraocular implant within said localized region of said eye.

* * * * *